United States Patent [19]
Vaughn

[11] Patent Number: 5,439,005
[45] Date of Patent: Aug. 8, 1995

[54] SURGICAL INSTRUMENT WITH TELESCOPING SLEEVE

[75] Inventor: William J. Vaughn, Fort Worth, Tex.

[73] Assignee: Midas Rex Pneumatic Tools, Inc., Fort Worth, Tex.

[21] Appl. No.: 25,085

[22] Filed: Mar. 2, 1993

[51] Int. Cl.⁶ ............................................. A61B 17/16
[52] U.S. Cl. .................................. 128/755; 606/180; 606/172; 279/42; 279/48; 408/240
[58] Field of Search ............... 606/167, 170, 172, 180, 606/190, 80; 128/755; 279/42, 48; 408/240, 239 R

[56] References Cited

U.S. PATENT DOCUMENTS

| | | |
|---|---|---|
| Re. 27,032 | 1/1971 | Hall . |
| 2,710,000 | 6/1955 | Kromer et al. ..................... 128/2 |
| 3,128,768 | 4/1964 | Geistauts . |
| 3,384,085 | 5/1968 | Hall . |
| 4,111,208 | 9/1978 | Leuenberger . |
| 4,512,344 | 4/1985 | Barber .............................. 128/755 |

Primary Examiner—Tamara L. Graysay
Attorney, Agent, or Firm—James E. Bradley

[57] ABSTRACT

A surgical instrument has a motor including a chuck for releasably receiving a dissecting tool for rotation about an axis of the surgical instrument. The dissecting tool has a cutting end and a shaft and the surgical instrument is provided with a base releasably connected to the motor. A sleeve is releasably connected to the base to support the shaft of the dissecting tool, and the surgical instrument is further provided with sleeve connection means for selectively permitting axial movement of the sleeve relative to the base and the dissecting tool to vary the amount of protrusion of the cutting end of the dissecting tool from the sleeve.

7 Claims, 4 Drawing Sheets

SURGICAL INSTRUMENT WITH TELESCOPING SLEEVE

BACKGROUND OF THE INVENTION

1. Field of the Invention

The present invention relates in general to surgical instruments for use in the dissection of bone or other tissue. More particularly, the present invention relates to sleeves or tubes for use in such tools and the means by which such sleeves or tubes are secured to the base or body of the surgical instrument.

2. Background Information

Surgical tools for use in the dissection of bone during surgical or other operations are conventional in the art. Many such tools employ pneumatic or electric motors to rotate dissecting tools or burrs to accomplish dissection operations.

In their most basic form, such surgical instruments comprise a motor portion, a base coupled to the motor, a dissecting tool for rotation by the motor, a sleeve to surround and support the dissection tool, and a means for connecting the sleeve to the base. Several prior-art surgical instruments are provided with sleeves that freely telescope and slide relative to both the base or body of the surgical instrument and the dissecting tool itself. Surgical instruments including such telescoping sleeves are disclosed in U.S. Pat. No. 2,710,000, Jun. 7, 1955, to Cromer et al.; U.S. Pat. No. 3,128,768, Apr. 14, 1964, to Geistauts; U.S. Pat. No. Re. 27,302, , Jan. 19, 1971, to Hall; and U.S. Pat. No. 4,111,208, Sep. 5, 1978, to Leuenberger.

In many conventional surgical instruments for the dissection of bone and the like, the sleeve is fixed with respect to the base or motor and the dissecting tool. In these types of surgical instruments, the shaft of the dissecting tool commonly is secured to the shaft of the motor by a chuck arrangement. A base or shroud, in turn, covers the chuck or collet arrangement to protect the user's fingers from exposure to the rotating chuck and shaft of the tool. The support sleeve, which laterally and rotationally supports and lends structural integrity to the otherwise flexible dissecting tool, is secured to the base. This design presents a substantial drawback when removal or replacement of the dissecting tool is desirable or necessary.

Generally, the base must be uncoupled from the remainder of the surgical instrument to permit access to the chuck or collet arrangement to release the dissecting tool. To expose the chuck or collet arrangement, the base and the sleeve secured to it must be slid outwardly along the shaft of the dissecting tool. Most conventional dissecting tools include a cutting head that is enlarged in diameter relative to the shaft of the tool, which prevents the sleeve and base from sliding over the cutting head and off of the shaft entirely. Because the outward movement of the base and sleeve is thus necessarily limited, a portion of dissecting tool shaft equal in length to the outward movement of the base and sleeve necessary to expose the chuck or collet arrangement must extend from the terminal end of the sleeve.

This protrusion of the dissecting tool beyond the end of the sleeve permits the dissecting tool to flex or deflect under load because the tool is insufficiently supported by the sleeve. In some cases, such as cutting along a curve, this flexibility is advantageous. In other cases, such as dissections calling for extreme precision, such flexibility can be a disadvantage. Also, such a large protrusion can also permit the end of the rotating dissecting tool to flail or whip, a transverse longitudinal vibration condition. The flail condition is not appropriate for certain dissections requiring precision cutting because flail can lead to inaccurate dissection, and dissection that is difficult to control in precision dissection operations.

A need exists, therefore, for a surgical instrument having a motor, a base, and a sleeve for supporting a dissecting tool, as well as means connecting the sleeve to the base that permits selective axial movement or telescoping of the sleeve relative to the base and the dissecting tool to vary the amount of protrusion of the enlarged cutting end of the dissecting tool from the sleeve, and that permits simple removal and replacement of dissecting tools and permits the user to vary the distance that the cutting end of the dissecting tool extends from the end of the sleeve.

SUMMARY OF THE INVENTION

It is a general object of the present invention to provide a surgical instrument wherein removal and replacement of the dissecting tool is facilitated. This and other objects of the present invention are accomplished by providing a surgical instrument having a motor including a chuck for releasably receiving the dissecting tool for rotation about an axis of the surgical instrument. The dissecting tool has a cutting end and a shaft and the surgical instrument is provided with a base releasably connected to the motor. A sleeve is releasably connected to the base to support the shaft of the dissecting tool, and the surgical instrument is further provided with sleeve connection means for selectively permitting axial movement of the sleeve relative to the base and the dissecting tool to vary the amount of protrusion of the cutting end of the dissecting tool from the sleeve.

According to a preferred embodiment of the present invention, the sleeve connection means comprises a collet secured to the base to receive the sleeve, and a collet nut in threaded engagement with the collet to selectively engage the collet about the sleeve to constrain the sleeve against axial movement relative to the base.

Other objects, features, and advantages of the present invention will become apparent with reference to the drawings and detailed description, which follow.

DESCRIPTION OF THE PREFERRED EMBODIMENT

Figure 1:
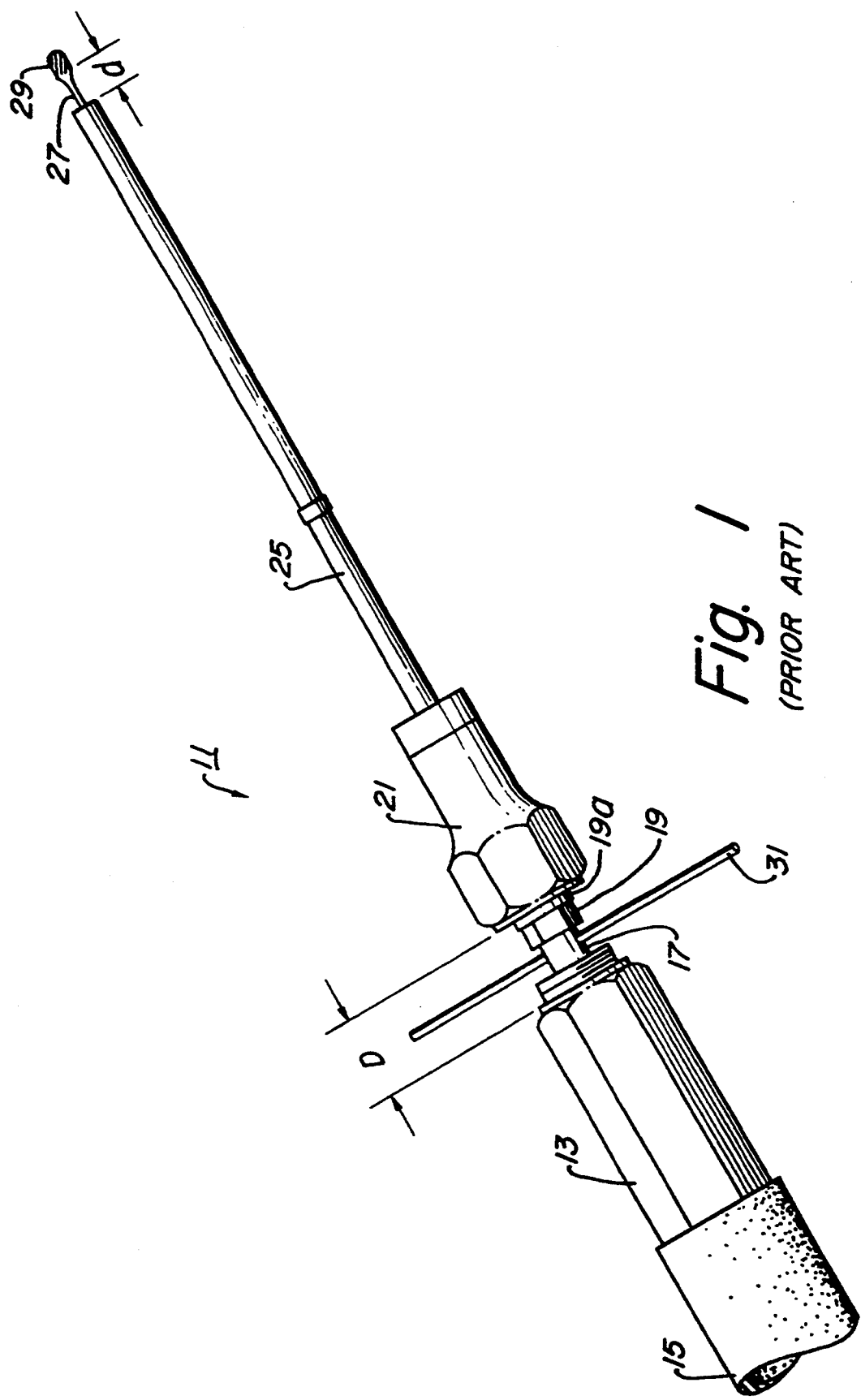
FIG. 1 is a perspective view of a prior-art surgical instrument.

Referring now to the Figures, and in particular to FIG. 1, a prior-art surgical instrument 11 is depicted in a partially disassembled mode of operation. Surgical instrument 11 comprises a fluid-driven motor 13, which is connected to a source of pressurized fluid by a fluid conduit 15. Motor 13 terminates at one end thereof in a rotatable shaft 17, which is rotated by motor 13 in response to fluid pressure. Shaft 17 terminates in a chuck 19, in this case a conventional collet arrangement including a collet nut 19a, which is secured by threads to a collet formed (not shown) on the end of shaft 17. Chuck 19 serves as a means to secure a dissecting tool to shaft 17 of motor 13.

A base 21 is releasably coupled to motor 13, in this case by threads. Base 21 functions as a shroud to cover chuck 19 and shaft 17 during operation thereby protecting the user from exposure to these moving parts.

A support sleeve 25 is secured to base 21. Support sleeve 25 serves to laterally and rotationally support and lend structural integrity to the otherwise flexible shaft 27 of a dissecting tool 29. Sleeve 25 is conventional in every respect, and includes a tubular member, which may contain bearings or the like to facilitate rotation of shaft 27 of dissecting tool 29 within sleeve 25.

In surgical instrument 11 depicted in FIG. 1, sleeve 25 is fixedly or immovably secured to base 21. More specifically, to disengage dissecting tool 29 from shaft 17 of motor 13, access to chuck assembly 19 must be had. To obtain such access, base 21 must be uncoupled from motor 13 and moved outwardly along shaft 27 of dissecting tool 29 a distance D. If dissecting tool 29 terminates in a cutting head larger in diameter than shaft 27 as shown, sleeve 25 cannot be moved beyond this cutting head. Therefore, even in the partially disassembled state illustrated in FIG. 1, enlarged cutting head of dissecting tool 29 must protrude beyond the end of sleeve 25 some distance d that must be greater than or equal to zero. Access to chuck 19 is necessary to permit insertion of anti-rotation rod 31 into a mating hole in rotatable shaft 17, to secure shaft 17 against rotation and to permit use of a wrench to loosen and tighten chuck 19.

Clearly then, upon recoupling base 21 to motor 13, enlarged cutting end of dissecting tool 29 will protrude from the end of sleeve 25 a distance equal to D+d. In conventional surgical instruments, the user cannot control or vary the amount of protrusion D+d because sleeve 25 is fixedly or immovably secured to base 21.

Figure 2:
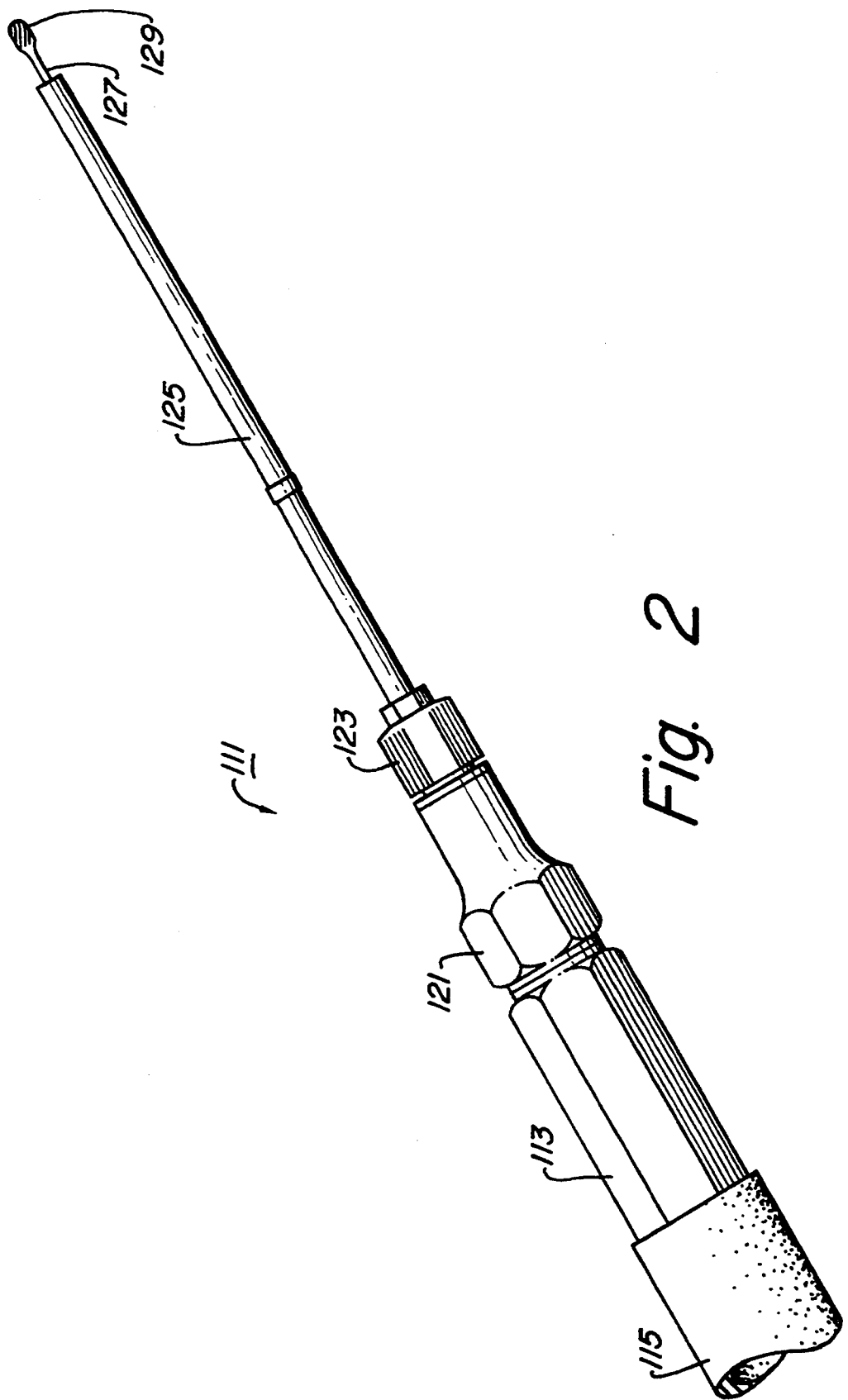
FIG. 2 is a perspective view of a the surgical instrument according to the present invention.

Referring now to FIG. 2, surgical instrument 111 according to the present invention is illustrated. Surgical instrument 111 is provided with a fluid-driven motor 113, which is in fluid communication with a source of pressurized fluid (not shown) through fluid conduit 115. A base 121 is coupled, in this case by internal threads, to an end of motor 113, and serves to cover the chuck assembly (not shown). A conventional sleeve 125 is movably secured to base 121 by means of a collet assembly 123. Sleeve 125 serves to laterally and rotationally support shaft 127 of dissecting tool 129.

Figure 3:
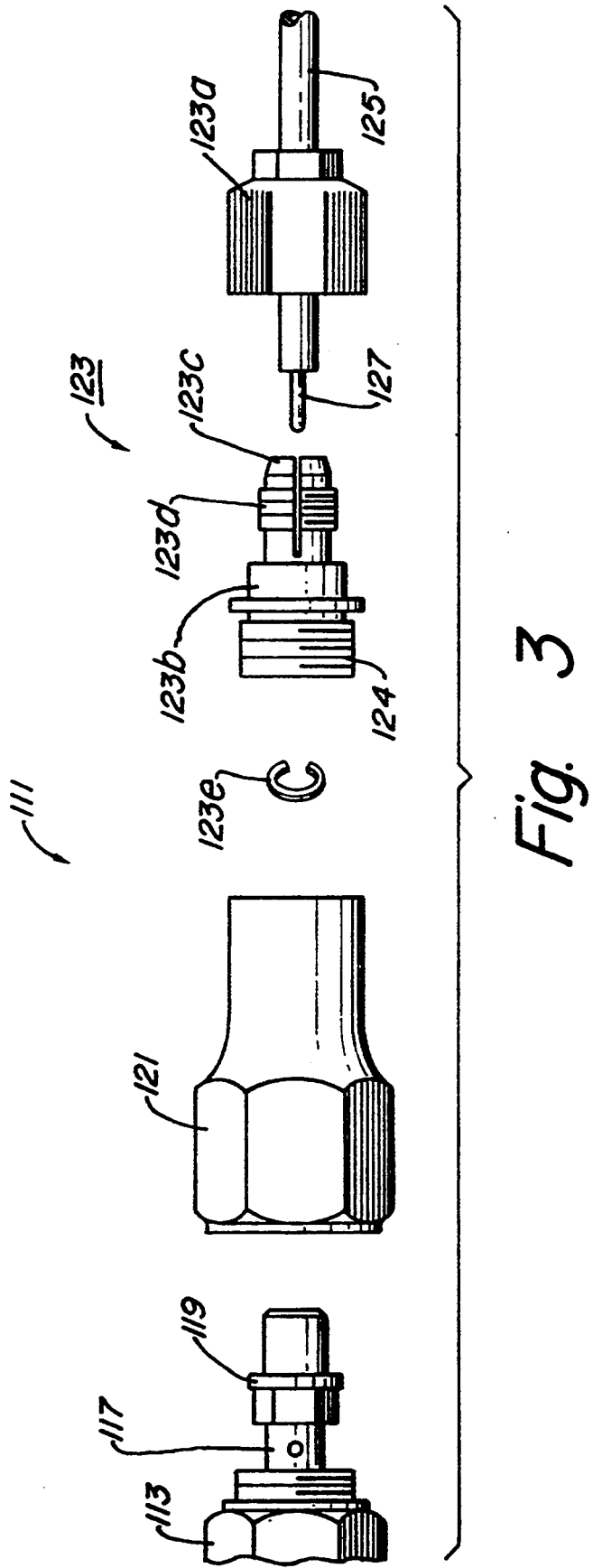
FIG. 3 is an exploded view of the component parts of the present invention, and depicts the interrelationship of the component parts.

FIG. 3 depicts an exploded view of surgical instrument 111, which illustrates the interrelationship of the component parts of surgical instrument 111, particularly the components of collet assembly 123. In FIG. 3, base 121 is shown uncoupled from motor 113 to expose rotatable shaft 117 and chuck assembly 119.

Collet assembly 123 is shown removed from base 121 to illustrate the component parts thereof. Collet assembly 123 includes collet nut 123a, which has a bore therethrough to accommodate sleeve 125, and is internally threaded for engagement with a collet 123b. Collet 123b defines a plurality of collet fingers 123c, which are exteriorly threaded at 123d for engagement with the internal threads of collet nut 123a. Collet 123b has a longitudinal bore therethrough to receive and engage the exterior of sleeve 125. Collet 123b is further provided with a lock ring 123e, which is received interiorly of the longitudinal bore through collet 123b and serves to limit the travel of sleeve 125 through the internal longitudinal bore of collet 123b. Collet 123b is secured to internal threads in base 121 by means of external threads 124.

Collet assembly 123 is selectively engageable about the exterior of sleeve 125 to permit selective axial movement of sleeve 125 relative to base 121 and shaft 127 of dissecting tool 129. Normally, shaft 127 of dissecting tool 129 is releasably engaged in chuck 119 and is constrained against axial movement relative to motor 113, shaft 127, and base 121. Collet assembly 123 is illustrated as only a preferred means for selectively permitting axial movement of sleeve 125 relative to base 121 and shaft 127 of dissecting tool 129, and for tightly securing sleeve 125 in a desired position.

Figure 4:
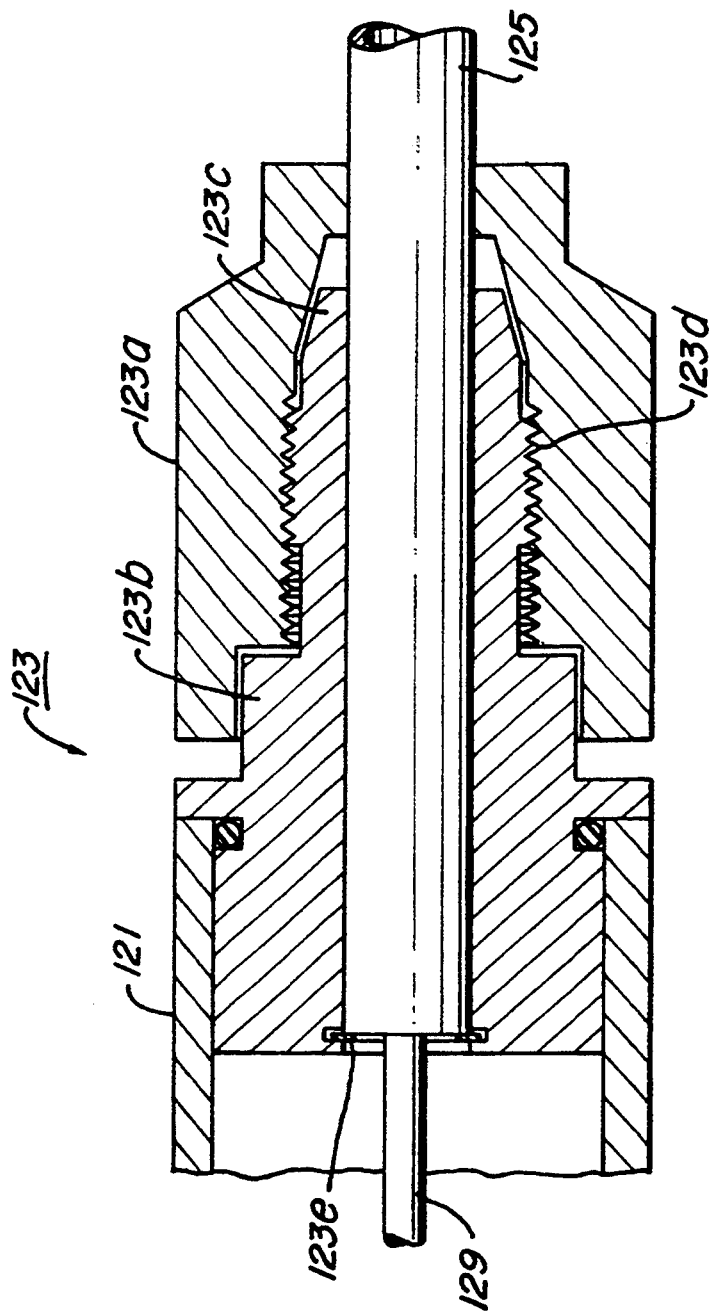
FIG. 4 is a partial longitudinal section view of a portion of the surgical instrument according to the present invention.

FIG. 4 is a partial longitudinal section view of the collet assembly 123 of FIG. 3, shown fully assembled. Collet assembly 123 is illustrated with collet nut 123a assembled over and fully tightened on threads 123d of collet 123b. Inclined surfaces on the interior of collet nut 123a and collet fingers 123c cooperate to permit collet fingers 123c to engage the exterior of sleeve 125 securely, thus preventing relative movement between sleeve 125 and collet assembly 123 and base 121. Sleeve 125 is shown fully retracted in base 121, wherein lock ring 123e or strap means abuts the end of sleeve 125 and prevents further inward movement of sleeve 125 within base 121. Shaft 129 of dissecting tool 127 extends from sleeve 125 into engagement with chuck (119 in FIG. 2), for rotation thereof by motor (113 in FIG. 2). Collet nut 123a may be loosened from engagement with collet fingers 123c to permit relative movement between sleeve 125 and base 121 in other modes of operation of the invention not illustrated herein.

With reference now to FIG. 2–4, the operation of surgical instrument 111 according to the present invention will be described. In normal dissecting operation, surgical instrument 111 is fully assembled as is generally depicted in FIG. 2. In this normal mode of operation, pressurized fluid is supplied from fluid conduit 115 to fluid-driven motor 113 for rotation of dissecting tool 129. Thus, bone may be dissected by application of rotating dissecting tool 129 to the area desired to be dissected.

At some point during dissection operation, it may become desirable to remove and/or replace dissecting tool 129, either because dissecting tool 129 has become dull, or because a dissecting tool of a different configuration is desirable. At this point, it is necessary to gain access to chuck 119 and shaft 117 to permit shaft 127 of dissecting tool 129 to be disengaged from chuck 119.

Collet assembly 123 is released by rotating collet nut 123a to disengage collet fingers 123c of collet 123b from frictional engagement with the exterior of sleeve 125. In this disengaged mode of operation, sleeve 125 may be moved axially inwardly within base 121 to increase the amount of shaft 127 of dissecting tool 129 that extends or protrudes beyond the end of sleeve 125. Normally sleeve 125 is fully retracted in base 121 until the end thereof abuts lock ring 123e of collet assembly 123.

After relative movement between sleeve 125 and base 121 is accomplished, base 121 is unscrewed from motor 113 to permit access to chuck assembly 119, preferably by unscrewing the threads therebetween. Base 121 then is moved outwardly from motor 113 and along and relative to shaft 127 of dissecting tool 129. The outward movement of base 121 relative to motor 113 exposes rotatable shaft 117 and chuck assembly 119. Sleeve 125 will move outward relative to shaft 127 along with base 121.

An anti-rotation rod (31 in FIG. 1) then is inserted through hole in shaft 117 to secure rotatable shaft 117 against rotation. A wrench or other similar tool then is engaged about chuck assembly 119 to loosen chuck and permit removal of dissecting tool 127 from engagement therewith. A new dissecting tool, or a tool of differing configuration, then is coupled to rotatable shaft 117 by engagement of chuck assembly 119 about the shaft of the dissecting tool. Base 121 then is recoupled to motor 113.

At this point, without further action, an undesirable length of the shaft of the new dissecting tool protrudes beyond the end of sleeve 125. Thus, sleeve 125 is extended axially outwardly from base 121 to eliminate or reduce the length of exposed and unsupported shaft of the dissecting tool (D+d in FIG. 1).

After the desired extension of sleeve 125 is accomplished, sleeve 125 may be secured or constrained against further axial movement relative to base 121 by engagement of collet assembly 123 with the exterior of sleeve 125. In the preferred embodiment of the present invention, such engagement is accomplished by tightening collet nut 123a about collet 123b, which in turn secures collet fingers 123c in frictional engagement with the exterior of sleeve 125, thereby constraining sleeve 125 against further axial movement relative to base 121. Dissecting operation then may be recommenced using surgical tool 111 according to the present invention.

The surgical instrument according to the present invention has a number of advantages. A principal advantage is that removal and replacement of dissecting tools for use with the surgical instrument is facilitated and expedited. Also, removal and replacement of dissecting tools may be relatively easily accomplished with a selected amount of extension or protrusion of the shaft of the dissecting tool beyond the end of the sleeve. Thus, a surgical instrument is provided that is more easily manipulated.

The present invention has been described with reference to a preferred embodiment thereof. Those skilled in the art will appreciate that the invention is thus not limited, but is susceptible to variation and modification without departing from the scope thereof.

I claim:

1. In a surgical instrument for use in dissecting tissue, the surgical instrument having a motor including a chuck for releasably receiving a dissecting tool for rotation of about an axis of the surgical instrument, the dissecting tool having a cutting end and a shaft, the surgical instrument having a base releasably connected to the motor, the improvement comprising:
   a sleeve releasably connected to the base, the sleeve having a longitudinal bore therethrough to rotatably receive and support the shaft of the dissecting tool; and
   sleeve connection for selectively permitting axial movement of the sleeve relative to the base and the dissecting tool to vary an amount of protrusion of the cutting end of the dissecting tool from the sleeve, the sleeve connection including:
   a collet secured to the base to receive the sleeve; and
   a collet nut in threaded engagement with the collet to selectively engage the collet about the sleeve to constrain the sleeve against axial movement relative to the base.

2. In a surgical instrument for use in dissecting tissue, the surgical instrument having a motor including a chuck for releasably receiving a dissecting tool for rotation of about an axis of the surgical instrument, the dissecting tool having a cutting end and a shaft, the surgical instrument having a base releasably connected to the motor, the improvement comprising:
   a sleeve releasably connected to the base, the sleeve having a longitudinal bore therethrough to rotatably receive and support the shaft of the dissecting tool; and
   a collet member secured to the base and defining at least one collet finger and a bore therethrough to receive the sleeve and to permit selective frictional engagement of the collet finger with the sleeve, wherein the sleeve is selectively axially movable relative to the base from an extended position to a retracted position and the sleeve is selectively maintained in a selected position by tightening the collet member about the sleeve.

3. The surgical instrument according to claim 2 wherein the collet member further comprises:
   a collet secured to the base to receive the sleeve, the bore of the collet having a selected length to define a distance from the extended position to the retracted position; and
   a collet nut in threaded engagement with the collet to selectively frictionally engage each collet finger with the sleeve to constrain the sleeve against axial movement relative to the base.

4. A surgical instrument for use in dissecting tissue, the surgical instrument comprising:
   a motor having a rotatable shaft and an axis;
   a dissecting tool having a cutting end and a shaft;
   a chuck connected to the rotatable shaft for releasably receiving the shaft of the dissecting tool for rotation of the dissecting tool about the axis of the motor;
   a base releasably connected to the motor and enclosing the chuck, the base being selectively removable from the motor to expose the chuck and the shaft of the dissecting tool;
   a sleeve releasably connected to the base and having a bore therethrough to rotatably receive and support the shaft of the dissecting tool;
   a collet secured to the base to receive the sleeve; and
   a collet nut in threaded engagement with the collet to selectively engage the collet about the sleeve to constrain the sleeve against axial movement relative to the base, wherein release of the collet nut permits axial movement of the sleeve relative to the base and the shaft of the dissecting tool to vary an amount of protrusion of the cutting end of the dissecting tool from the sleeve.

5. The surgical instrument according to claim 4 wherein the base is releasably connected to the motor by threads.

6. The surgical instrument according to claim 5 wherein the collet is provided with a stop means to limit the axial movement of the sleeve relative to the base and to define a retracted position of the sleeve relative to the base.

7. A method of replacing a dissecting tool having a cutting end and a shaft in a surgical instrument of a type having a motor, the motor having a chuck, which receives and secures the dissecting tool for rotation about an axis of the motor, a base releasably connected to the motor and enclosing the chuck, and a sleeve releasably connected to the base and having a bore therethrough to rotatably receive and support the dissecting tool, the method comprising the steps of:

providing a sleeve connection means for selectively permitting axial movement of the sleeve relative to the base and the dissecting tool;

releasing the sleeve connection means, wherein the sleeve is free to move axially relative to the base and the dissection tool;

retracting the sleeve relative to the base to a retracted position, wherein the cutting end of the dissecting tool protrudes a first selected distance from the sleeve;

releasing the base from connection with the motor to expose the chuck;

releasing the chuck to permit removal of the shaft of the dissecting tool therefrom;

replacing the dissecting tool with a second dissecting tool by inserting the shaft of the second dissecting tool through the bore in the sleeve and into the chuck, and tightening the chuck into engagement with the shaft of the second dissecting tool;

securing the base to the motor;

extending the sleeve relative to the base to an extended position, wherein the cutting end of the second dissecting tool protrudes a second selected distance from the sleeve, the second selected distance being less than that of the first selected distance; and actuating the sleeve connection means to constrain the sleeve against axial movement relative to the base.

* * * * *